United States Patent
Biering et al.

(10) Patent No.: US 6,649,162 B1
(45) Date of Patent: Nov. 18, 2003

(54) HEMOSTATIC SPONGE BASED ON COLLAGEN

(75) Inventors: Wolfgang Biering, Bergen (DE); Hamza Mansour, Paris (FR); Guenther Schlag, deceased, late of Vienna (AT), by Irmgard Schlag, representative; Thomas Seelich, Vienna (AT); Edgar Scheel, Hagen (DE); Georg Habison, Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/155,569

(22) PCT Filed: Apr. 2, 1997

(86) PCT No.: PCT/EP97/01662

§ 371 (c)(1),
(2), (4) Date: Mar. 29, 2001

(87) PCT Pub. No.: WO97/37694

PCT Pub. Date: Oct. 16, 1997

(30) Foreign Application Priority Data

Apr. 4, 1996 (AT) .............................. 611/96

(51) Int. Cl.$^7$ .............................. A61K 38/48
(52) U.S. Cl. ............ 424/94.64; 424/488; 128/DIG. 8; 128/DIG. 22
(58) Field of Search ................ 604/368, 304; 602/50, 900, 48; 264/49; 424/94.63, 400, 443, 423, 447; 128/DIG. 8, DIG. 22

(56) References Cited

U.S. PATENT DOCUMENTS

| | | | | |
|---|---|---|---|---|
| 3,514,518 A | * | 5/1970 | Charier-Vadrot | 34/305 |
| 3,823,212 A | * | 7/1974 | Chvapil | 128/DIG. 8 |
| 4,279,812 A | * | 7/1981 | Cioca | 106/156.21 |
| 4,292,972 A | * | 10/1981 | Pawelchak et al. | 264/50 |
| 4,390,519 A | * | 6/1983 | Sawyer | 128/DIG. 8 |
| 4,404,970 A | * | 9/1983 | Sawyer | 128/DIG. 8 |
| 4,407,787 A | * | 10/1983 | Stemberger | 106/122 |
| 4,409,334 A | * | 10/1983 | Lill et al. | 436/15 |
| 4,453,939 A | * | 6/1984 | Zimmerman et al. | 602/50 |
| 4,515,637 A | * | 5/1985 | Cioca | |
| 4,600,574 A | * | 7/1986 | Lindner et al. | 424/443 |
| 4,606,910 A | * | 8/1986 | Sawyer | 128/DIG. 8 |
| 4,696,812 A | * | 9/1987 | Silbering et al. | 128/DIG. 22 |
| 4,759,364 A | | 7/1988 | Boebel | 128/326 |
| 5,331,092 A | * | 7/1994 | Huc et al. | 435/174 |
| 5,567,806 A | * | 10/1996 | Abdul-Malak et al. | 128/DIG. 8 |
| 5,836,970 A | * | 11/1998 | Pandit | 602/48 |

FOREIGN PATENT DOCUMENTS

| | | | |
|---|---|---|---|
| DK | WO 90/13320 | * | 11/1990 |
| EP | 0 042 253 | * | 6/1980 |
| EP | 0090997 A2 | | 10/1983 |
| EP | 0 302 754 | * | 2/1989 |
| EP | 0 314 109 | * | 5/1989 |
| EP | 0372966 A2 | | 6/1990 |
| EP | 0372966 | * | 6/1990 |
| JP | 06159737 A | | 6/1994 |
| WO | WO90/13320 | | 11/1998 |

\* cited by examiner

Primary Examiner—Weilun Lo
Assistant Examiner—Linh Truong
(74) Attorney, Agent, or Firm—Heller Ehrman White & McAuliffe LLP

(57) ABSTRACT

The invention relates to a hemostatic sponge based on collagen and an activator or proactivator of blood coagulation homogeneously distributed therein, which is dried and contains a water content of at least 2%, preferably in the range of 2 to 25%, more preferred 10 to 20%, and a method for producing this sponge.

2 Claims, No Drawings

HEMOSTATIC SPONGE BASED ON COLLAGEN

The invention is related to a hemostatic sponge based on collagen and thrombin and a method for producing such a sponge as well as a wound coverage containing said sponge and a kit for preparing the wound coverage.

Biological glues based on coagulation factors of human or animal origin have long been known. A method for producing tissue adhesives based on fibrinogen an factor XIII has been described in U.S. Pat. Nos. 4,362,567, 4,298,598 and 4,377,572. The tissue adhesives are usually applied together with a separate component containing thrombin, which is enzymatically acting on fibrinogen to form fibrin, and on factor XIII to form the active factor XII Ia, which cross-links the fibrin to obtain a stable fibrin clot.

When applied to a large hemorrhaging area the tissue adhesives are usually applied on a collagen sheet before covering the wound with the sheet.

In U.S. Pat. No. 4,600,574 a tissue adhesive based on collagen combined with fibrinogen and factor XIII is described. This material is provided in the lyophilized form, ready for use. The fibrinogen and factor XIII are combined with the collagen by impregnating the collagenous flat material with a solution comprising fibrinogen and factor XIII, and lyophilizing said material.

The tissue sealing collagenic surgical dressing according to EP 0 049 469 is similarly prepared by combining collagen and fibrinogen and optionally an antibiotic through lyophilization.

Hemostatic sponges which are composed of natural bovine collagen are commercially available, e.g. Colgen® (IMMUNO AG), as wound coverage for a bleeding site. These products act on the intrinsic and extrinsic hemostatic pathways without forming a glue, which makes them rather slow-acting. However, their solid structure gives them mechanical strength.

When collagen is combined with fibrinogen and thrombin, such as described in EP 0 059 265, the material has to be carefully prepared by avoiding any water content. In the presence of minute amounts of water fibrinogen will be converted to fibrin and the material will no more be suitable for tissue sealing. Therefore, such a material is usually provided in a lyophilized form hematically packed together with a desiccant.

When fibrinogen in a hemostatic-sponge is avoided thrombin or a precursor therefore can be absorbed on a porous structure of biologically absorbable collagen according to WO 90/13320. This material is having a total water content of below 50% w/w. It is prepared by injecting an aqueous solution of thrombin or a precursor therefore together with thrombin stabilizing agents into the solid material at several sites. The thrombin stabilizing agents are preferably amino acids, PEG or polysaccharides. The relatively high water content results from the injection of the thrombin solution into the collagen sponge. Although the sponge can be dried at elevated temperatures, the drying is only moderate because of the risk of denaturation of the thrombin and collagen.

Due to the application of thrombin by injection, the distribution of thrombin in the sponge is highly inhomogenous which reduces the reproducibility and reliability of the wound coverage.

A homogeneous mixture of dispersible or soluble collagen with thrombin is prepared according to U.S. Pat. No. 4,515,637. The solution is then freeze-dried and rendered free of moisture yielding a storage-stable product. Although the dry collageneous sponges have high mechanic strength they turned out to be rather inflexible and thus could break when used by the surgeon. However, the drying to an absolutely moisture-free product was seen as essential for avoiding stability problems with thrombin.

The alternative use of a hemostatic collagen paste composition comprising an aqueous solution of thrombin is described in EP 0 372 966. This paste is packed in a squeeze tube or syringe package. The paste is however difficult to use for stopping bleeding in a large hemorrhaging area. When material of human or animal origin is applied to a patient there is a risk of transmitting pathogenic substances originated from the source material. Thrombin is usually derived from human or animal blood plasma carrying the risk of transmitting blood-born viruses, such as AIDS-virus, hepatitis virus and parvoirus. Therefore, measures are taken to inactivate any virus potentially present in plasma fractions, such as thrombin preparations. EP 0 541 507 describes a method for producing a virus-safe thrombin preparation derived from a human blood plasma fraction.

Collagen is usually treated by beta- or gamma-irradiation besides pretreating the collageneous source material with high concentrations of alkaline. These are common measures for inactivating any virus or prion potentially present in the source material.

A commercially available product, TachoComb®, which is produced by a method according to EP 0 059 265 is treated by gamma-irradiation after packing the prepared sheet. It turned out, that the irradiation treatment destroys the nativity of the fibrinogen. Denatured fibrinogen is hardly clottable. Therefore, this material is less effective than an in situ prepared combination of collagen and a tissue adhesive based on fibrinogen, which components are provided as a kit which is easily treated for virus inactivation separately.

It is the object of the present invention to provide a ready for use compress sponge containing resorbable collagen material, which does not have the above described disadvantages, especially with regard to the flexibility and mechanic stability of the material.

There is provided, according to the invention, a hemostatic sponge based on collagen and an activator or proactivator of blood coagulation homogeneously distributed therein. This sponge is provided in a dry form, which could be air-dried or lyophilized. However, it still contains a water content of at least 2%, preferably in the range of 2 to 25%. It is especially preferred that the water content is in the range between 10 and 20% in order to improve the storage stability at elevated temperatures.

It surprisingly turned out that the definite water content makes the sponge flexible, though maintaining its physico-chemical structure and mechanical strength.

It is also important to have the thrombin or a precursor of thrombin evenly distributed in the material in order to prevent local instability or hypercoagulability of the material. Despite of the water content the thrombin activity is surprisingly stable, probably because of the intimate contact of thrombin and collagen in the homogeneous mixture.

Nevertheless, thrombin stabilizers preferably selected from the group consisting of a polyol, a polysaccharide, a polyalkylene glycol, amino acids or mixtures thereof might be used according to the invention. The exemplary use of sorbitol, glycerol, polyethylene glycol, polypropylene glycol, mono- or disaccharides such as glucose or saccharose or any sugar or sulfonated amino acid capable of stabilizing thrombin activity is preferred.

The sponge is provided as a storage stable solid product, which is useful even after a storage of 6 months, preferable 2 years or even more years at room temperature.

Thrombin or the precursor of thrombin is understood as a protein that has thrombin activity and that induces thrombin activity when it is contacted with blood or after application to the patient, respectively. Its activity is expressed as thrombin activity (NIH-Unit) or thrombin equivalent activity developing the corresponding NIH-Unit. In the following thrombin activity is understood to comprise both, the activity of thrombin or any equivalent activity. A protein with thrombin activity might be selected from the group consisting of alpha-thrombin, meizo-thrombin, a thrombin derivative or a recombinant thrombin. A suitable precursor is possibly selected from the group consisting of: prothrombin, factor Xa optionally together with phospholipids, factor IXa, activated prothrombin complex, FEIBA, any activator or a proactivator of the intrinsic or extrinsic coagulation, or mixtures thereof.

The hemostatic sponge according to the invention might be used together with further physiologic substances. For example, the sponge preferably further comprises pharmacologically active substances, among them antifibrinolytics, such as a plasminogen-activator-inhibitor or a plasmin inhibitor or an inactivator of fibrinolytics. A preferred antifibrinolytic is selected from the group consisting of aprotinin or an aprotinin derivative, alpha-2-macroglobulin, an inhibitor or inactivator of protein C or activated protein C, a substrate mimic binding to plasmin that acts competitively with natural substrates, and an antibody inhibiting fibrinolytic activity.

As a further pharmacologically active substance an antibiotic, such as an antibacterial or antimycotic might be used together with the sponge according to the invention, preferably as a component homogeneously distributed in the sponge. Further combinations are preferred with specific enzymes or enzyme inhibitors, which may regulate, i.e. accelerate or inhibit, the resorption of the sponge. Among those are collagenase, its enhancers or inhibitors. Also, a suitable preservative may be used together with the sponge or may be contained in the sponge.

Although a preferred embodiment relates to the use of the collagen sponge which contains the activator or proactivator of blood coagulation as the only active component, further substances that influence the velocity of blood coagulation, hemostasis and quality of the sealing, such as tensile strength, inner (adhesive) strength and durability might be comprised. Procoagulants that enhance or improve the intrinsic or extrinsic coagulation, such as factors or cofactors of blood coagulation, factor XIII, tissue factor, prothrombin complex, activated prothrombin complex, or parts of the complexes, a prothrombinase complex, phospholipids and calcium ions, might be used. In case of a surgical procedure where a precise sealing is needed, it might be preferable to prolong the working period after the hemostatic sponge is applied to the patient and before clotting is effected. The prolongation of the clotting reaction will be ensured, if the sponge according to the invention further comprises inhibitors of blood coagulation in appropriate amounts. Inhibitors, such as antithrombin III optionally together with heparin, or any other serine protease inhibitor, are preferred.

The collagen of the sponge according to the invention is preferably of animal origin, preferably bovine or equine. However, also human collagen might be used in case of a hyper-sensitivity of the patient towards xenogenic proteins. The further components of the sponge are preferably of human origin, which makes the sponge suitable especially for the application to a human.

The medical field of indications for the sponge according to the invention is rather broad. The sponge not only can be used for stopping bleeding in very large hemorrhaging areas with a high blood pressure, but also for stopping oozing bleeding. The following internal or external surgical procedures are successfully carried out using the hemostatic sponge according to the invention: general surgery, for instance surgery of parenchymatous organs (liver, kidney, spleen, etc.), cardiovascular surgery, thoracic surgery, transplantation surgery, orthopedic surgery, bone surgery, plastic surgery, ear, nose and throat surgery, neurosurgery, surgery in urology and gynecology as well as haemostasis, such as in wound treatment.

The sponge might be provided in the form of a compress. In spite of the water content of the hemostatic sponge, it is capable of absorbing an extended amount of blood when applied to a wound. With the introduction of autologous or heterologous blood, fibrinogen or blood derivatives the blood coagulation is initiated and fibrin is formed to stop bleeding and seal the wound.

Moreover, the sponge according to the invention can be applied together with a fibrinogen preparation to the wound. Therefore, a kit is also provided to prepare a sponge or wound coverage before or directly in the course of during the application to the wound. The kit comprises besides the sponge at least a fibrinogen component, preferably in a storage stable form. The fibrinogen could be in the form of a fibrin sealant, such as a commercial product of a tissue adhesive based on fibrinogen, e.g. TISSEEL®(IMMUNO AG). Also, the further pharmacologically active substances, like mentioned above could be incorporated in the kit either in one or more components of the kit or as a separate component.

It has turned out, that the sponge preferably is characterized by a thickness of at least 3 mm, at least 5 mm up to 20 mm, depending on the indication. When the relatively thick flexible sponge is applied to a wound it is important that blood and fibrinogen can be absorbed throughout the sponge before fibrin is formed that might act as a barrier for the absorption of further wound secret. Therefore, the sponge according to the invention preferably contains a definite thrombin activity that ensures both the absorption of body liquid throughout the sponge and a fast acting effective sealing of the wound. It has proven, that 1000–10.000, preferably 5000–8000 Units/g are necessary for the effective hemostasis and treatment of wounds.

The preferred pH of the sponge according to the invention is in the range of 6 to 8. When a neutral pH is adjusted in a collageneous solution or gel there is the problem of collagen precipitation, which results in the formation of collagen fibers. It is not possible anymore to achieve an absolutely homogenous distribution of thrombin in the collagen-material in a suspension wherein collagen fibers have been formed. Thus, in order to obtain a homogeneous distribution of the activator or proactivator of blood coagulation one had to overcome the problem of fiber formation. The homogenous mixture is provived only when collagen remains in a soluble or gel date and optionally lyophilized or air-dried being in a gel state.

The inventive method of producing a sponge according to the invention comprises the acidification of a collageneous raw material to obtain a collagenic gel, wherein the collagen is provided in the dissolved state. The acidified material has a pH in the range of 1.5 to 4, preferably 2 to 2.5. It is preferred to use a weak acid, such as citric acid, for acidification. It surprisingly turned out, that the gel state is maintained without fiber formation even after neutralization, when a rigorous temperature control is applied at between 1 and 8° C., preferably 2 to 5° C. This low temperature prevents the precipitation of collagen, but must be maintained throughout all the stages of preparing the sponge before drying or lyophilization. The further components of the sponge can be admixed to obtain the homogeneous distribution either before or after the neutralization. The neutralization is carried out preferably by adding an alkali solution, such as NaOH or $Ca(OH)_2$.

A critical measure is the drying or lyophilization of the product, because a definite water content is needed at last. Preferably, the sponge can either be air-dried or lyophilized during a relatively short period, which provides for a residual water content in the above described range. An alternative procedure comprises the lyophilization to obtain a dry sponge, which is then moisturized by adding water or by a prolonged incubation in a medium with a relative humidity of more than 80% up to 100%. To facilitate the drying or lyophilization process it is preferred to incorporate a hydrophilic substance that is capable of retaining the specific water content after considerate and careful lyophilization or after actively absorbing the moisture. A preferred substance might be a polyol or a polysaccharide, which could also act protectively on labile components.

A specific embodiment relates to the sponge together with one or more further hemostatic layers of different structure and/or composition to obtain a composite wound coverage. The further layer might consist essentially of collagen to enhance the mechanic strength of the wound coverage. Preferably, further materials for combination are selected from the group consisting of modified or cross-linked collagen, modified cellulose, such as oxycellulose, human tissue and vicryl (Company Ethnor). The resulting wound coverage is preferably totally resorbable, but has nevertheless a high mechanic strength. Alternatively, it might also contain fibrinogen provided that the fibrinogen is not in a direct contact with thrombin. When thrombin and fibrinogen is to be used in a composite wound coverage according to the invention, it is preferred that a further layer of collagen is placed between the thrombin layer and the fibrinogen layer.

The wound coverage consisting of the sponge according to the invention and one or more further layers is preferably obtained by superimposing the sponge. Several hemostatic layers of a collagenic material might be prepared and afterwards side by side combined. Adherence of the layers by sequential or simultaneous freezing or lyophilizing, also known as co-freezing or co-lyophilization is preferred. Further combinations methods comprise cross-linking or glueing. The various layers can be prepared by cooling the sponge according to the invention below 0° C., preferably between –10° C. and –1° C., and spraying or floating a liquid containing the liquid which forms a superimposed or juxtaposed layer upon further freezing and/or lyophilizing.

For lyophilization the mixture of collagen and further components is preferably brought in a definite shape whereby specific dimensions of a sheet are obtained. Exemplary forms are pads and patches, sheets, cubes, tubes, cones and fibres, which can be pressed or formed to the desired structure. The structure may comprise wholes or may be permeable to air.

It is further preferred to use a specific collagen type selected from the group consisting of type I, II, III, IV, VII and X. Type IV is especially peferred when human collagen is used. Besides native collagen fragmented or enzymatically treated collagen, e.g. pepsin or pectin treated collagen may be used.

The structure and mechanic strength of the collagenic layers are further characterized by its concentration. It is preferred to prepare the sponge with a collagen concentration of 1 to 15 $mg/cm^3$.

It is preferred to prepare the combination of collagen and blood coagulation factors in presence of a small quantity of collagen, reflected by a concentration of 1 to 2 $mg/cm^2$. During freeze-drying the combination aquires then a supporting structure and an appearance similar to that of pure lyophilized collagen.

The lyophilized sponge according to the present invention is preferably off-white colored looking like cotton wool that is flexible and strong.

The air-dried sponge mostly is quite transparent.

For reasons of sterilization the sponge according to the invention is preferably sterilized by irradiation, more preferably after it is dried, by $\beta$- or $\gamma$-rays of the appropriate energy and wavelength. Besides the sponge it is also possible to irradiate the source material, which is the collageneous fraction in a solid form. The collageneous raw material may therefore be provided as a collagen powder, ready for sterilization by irradiation.

According to a specific embodiment the components of the sponge are treated separately to inactivate any pathogen potentially present, preferably using a chemical and/or physical treatment, preferably a heat treatment, such as according to EP 0 159 311. Anyway it is preferred to additionally sterilize the prepared sponge by conventional means.

The invention is further illustrated by, but is not to be limited to the following examples.

EXAMPLE 1

Preparation of a Collagen Gel

The equalent of 1 g of dry collagen (from liquid, pasty, fibrous or powdery collagenous material) were dissolved in 100 ml of 0.01 M citric acid. The mixture was shaken until a uniform and fluid gel was produced. The pH was adjusted to 7.2 by adding a 1 NaOH solution, while continuously stirring at 4° C. This gel contained 1% collagen. Equally, a 0.25% collagen gel was produced.

EXAMPLE 2

Preparation and Lyophilization of a Collagen Gel Containing Thrombin 60 ml of 1% collagen gel obtained according to example 1 was mixed with 5 ml of 1000 IU/ml thrombin solution (HUMAN THROMBIN, IMMUNO AG) at 4° C. The homogenous mixture was poured onto a 10×10 cm tray previously cooled to 4° C. The tray was transferred into the freezer compartment of a freeze dryer, previously cooled to 4° C. Then the freezer cycle was started down to –20° C. and the product was freeze-dried until a 15% water content was obtained.

The product was a flexible cotton-like fleece, which was cut to the desired dimensions. The fleece had the following characteristics.

Product I

| | |
|---|---|
| Collagen: | 8.55 $mg/cm^2$ |
| Thrombin: | 50 $IU/cm^2$ |
| Dimensions: | 10 × 10 |
| Thickness: | 0.6 cm |

EXAMPLE 3

Preparation of a Wound Coverage Containing Several Layers 60 ml of 1% collagen gel obtained according to example 1 was poured onto a 10×10 cm tray previously cooled to 4°

C. The tray was transferred into a freezer compartment of a freeze-dryer previously cooled to 4° C. The freezer cycle was started down to −5° C. and the product was frozen at −5° C.

Thereafter, 20 ml of 0.25% collagen gel obtained according to example 1 was mixed with 5 ml of 1000 IU/ml thrombin solution (HUMAN THROMBIN, IMMUNO AG) and stirred at 4° C. to obtian a homogenous mixture. The mixture was poured uniformly on the top of the frozen collagen sheet, which still laid in the tray, and was previously frozen at −5° C. The tray was quickly returned into the freeze-dryer and the freezer cycle was started down to −20° C. The freeze-drying took place until the final desorption temperature of 25° C. to 30° C. was reached. The product contained a 14% water content. The resulting product was composed of 2 strongly adhering layers and was easy to cut and package. The product had the following characteristics:
Product II

| First layer: | |
| --- | --- |
| Collagen: | 8.55 mg/cm$^2$ |
| Dimensions: | 10 × 10 cm |
| Thickness: | 0.6 cm |
| Second layer: | |
| Collagen: | 1.7 mg/cm$^2$ |
| Thrombin: | 50 IU/cm$^2$ |
| Dimensions: | 10 × 10 cm |
| Thickness: | 0.2 cm |

A superimposed layer of fibrinogen combined with a low concentration of collagen was prepared as follows: 20 ml of 0.25% collagen gel obtained according to example 1 was mixed with 6.5 ml of 80 mg/ml fibrinogen solution (HUMAN FIBRINOGEN, IMMUNO AG) at 4° C. The mixture was poured uniformly on the top of the frozen collagen-thrombin sheet, which was provided in a tray, previously frozen at −5° C. The tray was transferred into the freezer compartment of a freeze-dryer and the freezer cycle was started down to −20° C. The final desorption temperature was 20° C. to 30° C., the final water content was about 15%. The resulting product was composed of 3 strongly adhearing layers and was easy to cut and package. The product had the following characteristics:
Product III

| First layer: | |
| --- | --- |
| Collagen: | 8.55 mg/cm$^2$ |
| Dimensions: | 10 × 10 cm |
| Thickness: | 0.6 cm |
| Second layer: | |
| Collagen: | 1.7 mg/cm$^2$ |
| Thrombin: | 50 IU/cm$^2$ |
| Dimensions: | 10 × 10 cm |
| Thickness: | 0.2 cm |
| Third layer: | |
| Collagen: | 1.7 mg/cm$^2$ |
| Fibrinogen: | 10 mg/cm$^2$ |
| Dimensions: | 10 × 10 cm |
| Thickness: | 0.2 cm |

This manufacturing process can be used for manufacturing a compress sponge composed of a variety of collageneous layers and the order of the layers can be changed according to the desired degree of effectiveness. Using this process products with the following characteristics were obtained:

A mixture of 20 ml of 0.25% collagen gel and 5 ml of 1000 IU/ml thrombin solution and 1 ml of 40 M calcium chloride solution was stirred at 4° C. and a frozen collagen layer was prepared as described above. The freezer cycle was started down to −5° C. for 1 hour. The next layer was prepared as described above using 20 ml of 0.25% collagen gel, whereby the freezer cycle was maintained down to −5° C. A further layer was prepared using 20 ml of 0.25% collagen gel in a mixture with 6.5 ml of the 80 mg/ml fibrinogen solution. During freeze-drying a final desorption temperature of 20° C. to 30° C. was obtained. The product had the following characteristics.
Product IV

| First layer: | |
| --- | --- |
| Collagen: | 1.77 mg/cm$^2$ |
| Thrombin: | 50 IU/cm$^2$ |
| Dimensions: | 10 × 10 cm |
| Thickness: | 0.2 cm |
| CaCl$_2$: | 1 ml of a 40 mmol/l solution |
| Second layer: | |
| Collagen: | 1.7 mg/cm$^2$ |
| Dimensions: | 10 × 10 cm |
| Thickness: | 0.2 cm |
| Third layer: | |
| Collagen: | 1.7 mg/cm$^2$ |
| Fibrinogen: | 10 mg/cm$^2$ |
| Dimensions: | 10 × 10 cm |
| Thickness: | 0.2 cm |

EXAMPLE 4

Application of the Sponge in the Pig Model and Comparison to the Commercially Available Product (TachoComb®)

Using a liver resection model in heparinized pigs a comparison was made between product I, obtained according to example 2, a collagen product without a thrombin content and TachoComb® (Nycomed).

When the collagen product was used, there was no hemostasis leading to bleeding to death. There was no hemostasis either when TachoComb® was used. Discontinuation of the resection surface was observed, whereby rebleeding started and the pigs bled to death.

When product I was used hemostasis was complete within 5 minutes. The pigs were postoperatively observed for 3 days. Thereafter they were sacrificed. Upon autopsy there was no blood found in the abdominal cavity.

What is claimed is:

1. A hemostatic sponge comprising (a) collagen, (b) at least one water content stabilizer selected from the group consisting of polysaccharides and polyols and (c) at least one component selected from the group consisting of thrombin and a precursor of thrombin, wherein (i) the component is homogeneously distributed in the sponge wherein the (ii) the sponge has been lyophilized and contains a water content no less than 2%.

2. A method for producing a hemostatic sponge comprising collagen and at least one component selected from the group consisting of a thrombin and a precursor of thrombin, wherein (i) the component is homogeneously distributed in the sponge and (ii) the sponge is dried and contains a water content of no less than 2%, comprising
    acidifying a collagenous raw material to obtain a collagen gel,
    mixing the gel with the component to obtain a homogenous mixture, wherein the mixture is lyophilized in the presence of a substance that retains water and
    drying the mixture to a water content of no less than 2%.

* * * * *